United States Patent [19]

Jennings et al.

[11] 4,263,224
[45] Apr. 21, 1981

[54] ACRYLONITRILE DIMERIZATION PROCESS

[75] Inventors: James R. Jennings, Hutton Rudby; Ross J. Cozens, Liverpool; Michael J. Lalkham, Runcorn, all of England

[73] Assignee: Imperial Chemical Industries Limited, London, England

[21] Appl. No.: 58,544

[22] Filed: Jul. 17, 1979

[30] Foreign Application Priority Data

Jul. 26, 1978 [GB] United Kingdom ............... 31253/78

[51] Int. Cl.$^3$ ................... C07C 120/00; C07C 121/30
[52] U.S. Cl. ............................................. 260/465.8 D
[58] Field of Search ................................. 260/465.8 D

[56] References Cited

U.S. PATENT DOCUMENTS

| | | | |
|---|---|---|---|
| 4,126,632 | 11/1978 | Hogan et al. | 260/465.8 D |
| 4,138,428 | 2/1979 | Jennings et al. | 260/465.8 D |

OTHER PUBLICATIONS

Clark et al., Quarterly Reviews, 18, (1964), pp. 295–320.
Hidai, et al., Aspects of Homogeneous Catalysis, vol. 2, (1974), pp. 159–188.
Dietsche, Tetrahedron Letters, No. 51, pp. 6347–6351, (1966).

Primary Examiner—Joseph P. Brust
Attorney, Agent, or Firm—Cushman, Darby & Cushman

[57] ABSTRACT

A process for the dimerization of acrylonitrile to predominantly straight-chain $C_6$ dimers, in which the acrylonitrile is dissolved in an organic solvent capable of donating protons, the acrylonitrile and solvent being substantially dry, and the solution contacted with a catalyst comprising a phosphorus (III) compound of general formula:

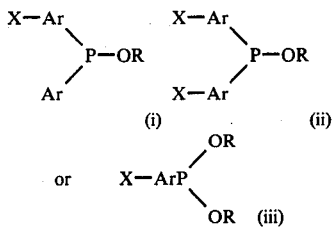

where Ar is an aromatic nucleus and where groups X, which may be the same or different, are electron-donating substituents of the aromatic nucleus which give rise to a negative Hammett $\sigma$ constant, and R represents a hydrocarbyl group, the acrylonitrile and solvent being contacted with a low-cost scavenging reagent for a predetermined period of time before being contacted with the aforementioned catalyst.

6 Claims, 2 Drawing Figures

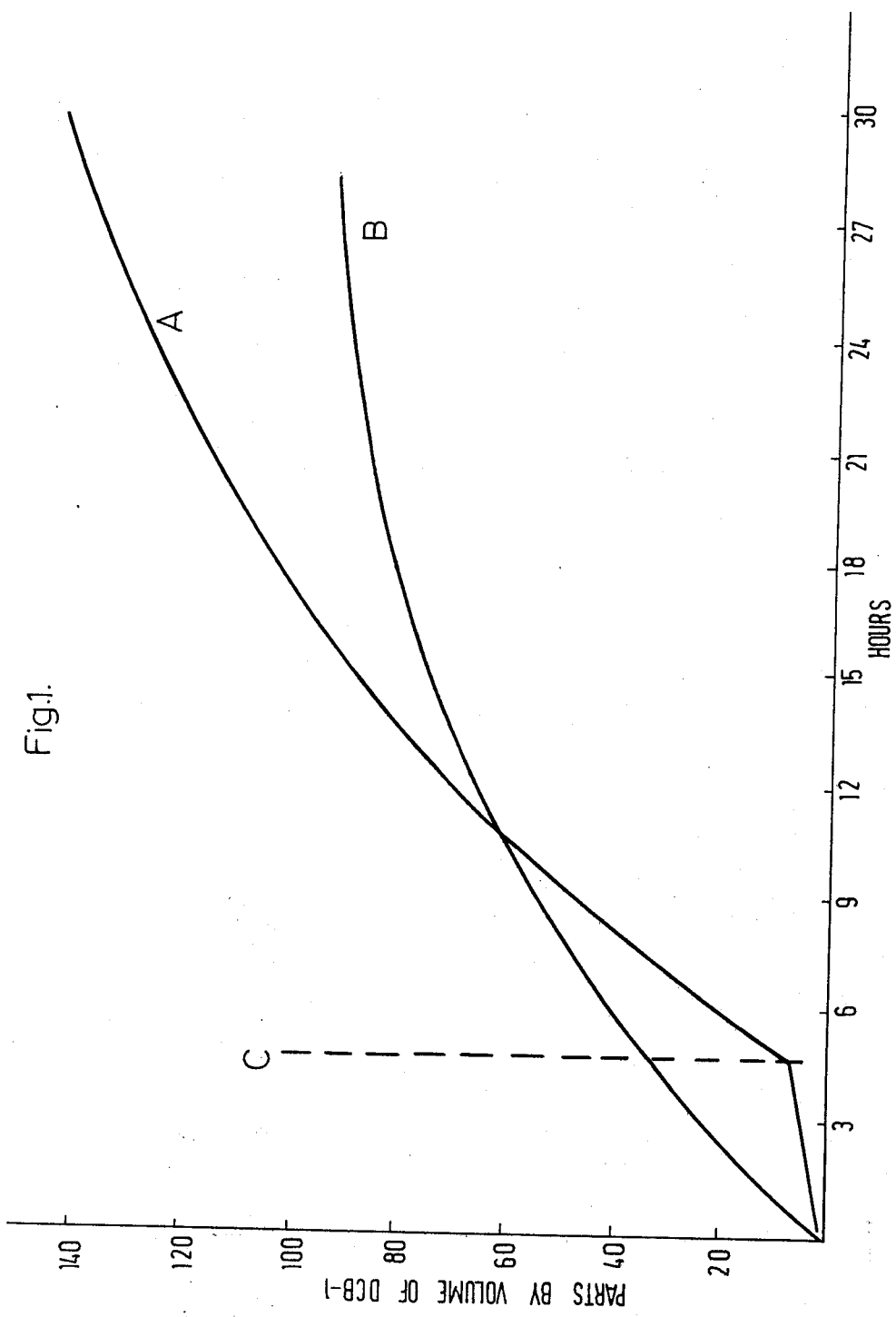

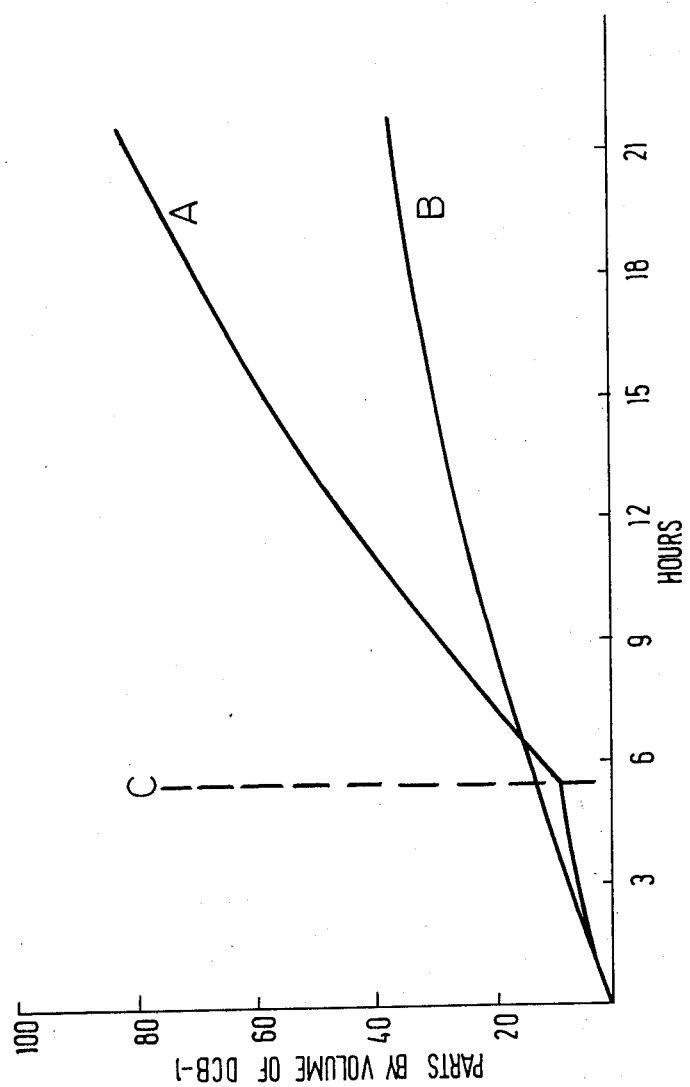

ACRYLONITRILE DIMERIZATION PROCESS

This invention relates to a dimerisation process and especially to a process for the dimerisation of acrylonitrile to linear $C_6$ dinitriles.

In our co-pending British application Nos. 45324/75 and 52888/75 (published as German OLS No. 2649904) we describe and claim a process for the dimerisation of acrylonitrile to predominantly straight-chain $C_6$ dinitriles in which the acrylonitrile is contacted with an organic phosphorus (III) compound which has at least one hydrocarbyl and at least one alkoxy or cycloalkoxy group attached to the phosphorus atom or atoms, the acrylonitrile being dissolved in an organic solvent capable of donating protons, for example, a hydroxylic solvent such as an alcohol, the acrylonitrile and solvent being substantially dry.

Furthermore, in our co-pending British patent application No. 15029/77 (published as German OLS No. 2747139) we describe a modification of the above process in which the phosphorus compound catalyst is one having a formula

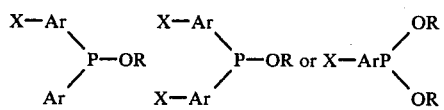

where R represents a hydrocarbyl group, Ar represents an aromatic nucleus and groups X are electron-donating substituents which give rise to a negative Hammett $\sigma$ constant. Suitable substituents include alkoxy, dialkylamino and alkylamino groups. The use of the abovementioned substituted aryl phosphorus compounds gives rise to an enhanced rate of dimer formation; but this advantage tends to be off-set by the greater cost of production of the compounds.

It has been observed that there is often an unduly high consumption of catalyst in the initial period of the dimerisation process, thought, without prejudice, to be due to de-activation of the catalyst compound by traces of residual impurities, e.g. water and/or carbonyl compounds, in the acrylonitrile and/or solvent(s), despite their rigorous drying and purification. We have now found that by using a comparatively cheap scavenging reagent in the initial period of the reaction and subsequently adding the more expensive substituted aryl phosphinite or phosphonite, greatly enhanced utilisation of the expensive catalyst may be obtained.

According to the present invention, we provide a process for the dimerisation of acrylonitrile to predominantly straight-chain $C_6$ dimers, in which the acrylonitrile is dissolved in an organic solvent capable of donating protons, the acrylonitrile and solvent being substantially dry, and the solution contacted with a catalyst comprising a phosphorus (III) compound of general formula

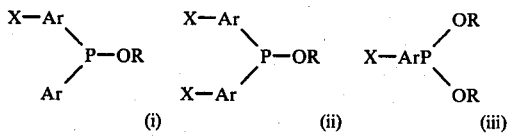

where Ar is an aromatic nucleus, e.g. phenyl or naphthyl, and where groups X, which may be the same or different, are electron-donating substituents of the aromatic nucleus which give rise to a negative Hammett $\sigma$ constant, and R represents a hydrocarbyl group, the acrylonitrile and solvent being contacted with a low-cost scavenging reagent (as hereinafter defined) for a predetermined period of time before being contacted with the aforementioned catalyst.

By a "scavenging reagent" we mean a compound which will react with any residual traces of water or other catalyst-deactivating impurities in the reaction mixture, but does not adversely affect the principal dimerisation reaction. By a "low-cost" scavenging reagent we mean that the scavenging reagent should be one which is substantially less expensive than the catalyst compound.

Substituents X may be in the para or meta positions; but are preferably para.

A discussion on Hammett $\sigma$ constants and a table showing values for most common substituents is to be found in an article by Clark and Perrin in Quarterly Reviews, Vol. 18, 1964 pp. 295-320.

Examples of suitable substituents X include alkoxy groups, e.g. methoxy, ethoxy, i-propoxy and t-butoxy; alkyl groups, e.g. methyl, ethyl and propyl; and alkylamino groups, e.g. dimethylamino and diethylamino. It is of course, essential that group X should be one which does not react adversely with the components of the reaction system.

Suitable hydrocarbyl groups R include alkyl or cycloalkyl groups such as methyl ethyl, i-propyl, neopentyl, 2-ethylhexyl and cyclohexyl.

The catalyst compound is preferably a phosphinite, that is a compound of formulae (i) or (ii) above, because such catalysts have a longer lifetime than the equivalent phosphonites.

Examples of suitable scavenging reagents include aryl phosphonites and phosphinites, that is, compounds which contain one or two alkoxy or cycloalkoxy groups and two or one aryl groups attached to the phosphorus atom. Such compounds may be prepared by reacting phosphorus trichloride with an aromatic hydrocarbon under Friedel-Crafts conditions, followed by alcoholysis of the product. However, phosphonite scavenging reagents are preferred, since these are more easily accessible by the Friedel-Crafts route. Furthermore, phosphonites themselves are dimerisation catalysts and those having alkyl groups attached to the phosphorus atom tend to give a higher proportion of branched dimer, which we wish to avoid. Examples of suitable phosphonites include dialkyl phenylphosphonites, for example, dimethyl phenylphosphonite, and dialkyl tolylphosphonites, for example dimethyl tolylphosphonite. For the sake of simplicity, the scavenging reagent will hereinafter be characterised by phosphonite only.

The period of time before the catalyst is added to the reaction mixture is dependent on the time taken for the phosphonite to react with all the residual impurities. This may be readily determined by adding an appropriate quantity of phosphonite to the solution of acrylonitrile in proton-donating solvent and heating it to the desired reaction temperature. The concentration of phosphonite in the mixture is then monitored by $^{31}P$ nuclear magnetic reasonance (NMR) analysis to determine the time taken for phosphonite concentration to fall to a small, approximately constant, value. It will be appreciated that if the concentration of phosphonite falls to zero, there may still be some harmful impurities remaining in the solution. Thus the amount of phosphonite initially added must be sufficient to react with all the impurities. This is most readily achieved by adding a small excess of phosphonite. An excess of phosphonite is not in itself detrimental to the process and enhances the rate of removal of catalyst deactivating impurities. However, a large excess of phosphonite would reduce the cost advantage gained, because the excess phosphonite would be wasted. The concentration of unreacted phosphonite may be determined by $^{31}P$ N.M.R. The optimum amount of phosphonite which should be added will depend mainly upon the amount of residual catalyst deactivating impurities (e.g. water and hydroquinone) remaining in the acrylonitrile/solvent mixture after drying and removal of stabilisers from the acrylonitrile, as described in detail below. However, using the drying techniques described below we find that an addition in the range 0.02 to 0.1% by volume of phosphonite (calculated on total volume of the acrylonitrile/solvent mixture) is generally satisfactory.

The presence of an organic solvent is essential to our process, since in the absence of solvent rapid polymerisation of the acrylonitrile occurs. Suitable solvents are proton-donating solvents which are substantially unreactive in respect of addition to, or reaction with, the unsaturated linkage of the acrylonitrile or the products of acrylonitrile dimerisation. Furthermore, the solvent must not react with the phosphorus compounds or catalytic intermediates to form inactive phosphorus species at such a rate as to seriously impair the dimerisation reaction. For example, phenols have been found to be unsuitable in this respect. The organic solvent must be rigorously dried, so as not to adversely affect catalyst lifetime.

Preferably hydroxylic solvents, such as alcohols, are used, provided always that they do not react adversely with the phosphorus compound or any intermediates it may form with acrylonitrile. This may be readily established by experiment. Tertiary and secondary alcohols are preferred, for example t-butanol, 2-butanol and isopropanol.

Isopropanol may be advantageous with the catalysts of the present invention in that it tends to promote faster reaction and enhance selectivity to straight-chain dimers. On the other hand t-butanol may cause evolution of isobutene via butoxy phosphorus compounds, leading to catalyst decay.

The concentration of proton-donating solvent is generally in the range 0.1 to 50% by volume, calculated on the total volume of the reactants; but the optimum concentration will vary with the precise nature of the solvent and the catalyst compound. The molar concentration of proton-donating solvent will generally be greater than the molar concentration of the catalyst.

In order to reduce the amount of hexamer and/or other oligomers or polymers (hereafter referred collectively as polymeric by-products or merely polymers) which may be co-produced with the desired dimeric products, it is often desirable to add a non-hydroxylic co-solvent to the reaction mixture used in our process. It will be apparent that the co-solvent must be dried to a level which maintains the overall anhydrous state of the system.

Suitable non-hydroxylic organic solvents include hydrocarbons, for example, hexane, cyclohexane, toluene, and petroleum ethers; ether, for example, tetrahydrofuran, diethyl ether and diisopropyl ether; and nitriles, for example, acetonitrile, propionitrile; and fluorobenzenes. They hydrocarbon co-solvents are generally preferred.

An essential feature of the present invention is that the reaction must be conducted in the substantial absence of water. Without prejudice to our invention, we believe that the water reacts with the catalyst and, of course, low cost phosphonite in the presence of acrylonitrile and/or dimeric products to give non-catalytic phosphorus (V) addition compounds. Thus, the acrylonitrile proton-donating solvent and co-solvent must be dried before use, otherwise the quantity of catalyst and/or low-cost phosphonites required to effect dimerisation may have to be increased to a commercially unacceptable level. In particular acrylonitrile, which commonly contains as much as 4000 ppm of water, even after distrillation, must be rigorously dried. It is also noted that hydroquinone stabilisers, which are present in acrylonitrile as supplied should be removed. Any suitable drying technique may be used, provided that the final water level is sufficiently low. For example, acrylonitrile and hydroxylic solvents may be dried by being contacted with calcium hydride or a 3A or 4A molecular sieve. The above findings contrast strongly with the teaching of the prior art which makes no mention of removal of water and/or hydroquinone stabilisers, and in many instances advocates the addition of water and stabilisers, such as hydroquinone, to the reaction mixture.

Generally the concentration of acrylonitrile in the solvent or solvent mixture should range from 5 to 75% by volume. The concentration of acrylonitrile is kept as high as possible in order to optimise throughput and thus concentrations in the range 10 to 50% by volume are generally preferred.

The concentration of the catalyst in the reaction mixture, may be varied over a wide range, for example, from 0.001 to 1% by volume, preferably 0.01 to 0.1% calculated on the volume of liquid reactants. When present, the proportion of co-solvent in the reaction mixture may be varied over wide limits. In general the ratio of proton-donating solvent to co-solvent is in the range 1/40 to 40/1; but ratios at the lower end of the range are generally preferred. However, the final choice of solvent/co-solvent ratio will depend on how it is desired to run the process and the catalyst compound used. For example ratios in the 1/5 to 1/20 give rise to enhanced catalyst lifetime and increased selectivity to linear dimer, when compared with an equivalent reaction where the ratio is 1/1.

Changes in the ratio of proton-donating solvent/co-solvent are generally reflected by changes in the amount of polymers formed and changes in the reaction rate. These changes in reaction parameters are often dependent upon the actual catalyst and solvent system chosen.

The ratio of linear to branched dimers is dependent on the solvent/co-solvent ratio in some instances. It is sometimes found that, as the proportion of proton-donating solvent decreases, the proportion of linear dimer increases, and vice-versa.

The reaction temperature is commonly in the range 0° to 180° C.; but it may be preferred to keep the range temperature below 75° C. to minimize undesirable side reactions. It is noted that the reaction will proceed below 0° C., maintaining selectivity, but at a reduced rate. In fact, in some cases improved selectivity may be obtained at lower temperatures.

Unlike other acrylonitrile dimerisation processes, the presence of compounds such as hydroquinone and its monomethyl ether, p-methoxyphenol, which are commonly used at present as acrylonitrile stabilisers, should be avoided.

The reaction may be carried out batchwise or continuously. In the latter case it may be convenient to support the catalyst compound or to use a polymeric tervalent phosphorus compound to enable the reaction to be carried out in the liquid phase using a heterogeneous catalyst.

The dimeric products of our invention are predominantly linear $C_6$ dinitriles, especially the 1,4-dicyanobutenes (1,4 DCB-1). Selectivities >90 wt % (calculated on total dimeric product) may be readily obtained.

The desired products may be readily separated from the reaction mixture for example by fractional distillation or solvent extraction.

The invention will be illustrated by the following Example, in which all parts are by volume.

The acrylonitrile was dried before use by means of calcium hydride. This was accomplished by adding powdered calcium hydride to the acrylonitrile overnight, then decanting the acrylonitrile on to fresh calcium hydride powder and refluxing for 150 minutes. The acrylonitrile was then distilled from the calcium hydride. Water levels were found to be in the range 30-80 ppm after this procedure. The acrylonitrile was dried finally by storing over freshly activated 3A molecular sieve to give levels below 15 ppm.

The phosphorus (III) compounds used are either commercially available or were prepared using methods given in "Organo-Phosphorus Compounds", Kosolapoff and Maier, published by Wiley 1972, Vol 4, Chapters 10 and 11.

All analyses of dimeric products were made by gas-liquid chromatography (g.l.c.)

EXAMPLE 1

Acrylonitrile (540 parts) was added to a mixture of toluene (1800 parts) and isopropanol (180 parts) under rigorously anhydrous conditions. Dimethyl phenylphosphonite (1.0 part) was added as a scavenging reagent and the mixture heated to 60° C.

After about 4.5 hours, the catalyst, isopropyl bis (para)methoxyphenylphosphinite (1.1 parts) was added to the mixture and the temperature maintained at 60° C. After about 25 hours 130 parts of 1,4 dicyanobutene-1 (DCB-1) had formed and $^{31}P$ MNR analysis showed that about 25% of the catalyst had been consumed, corresponding to a catalyst usage of about 480 parts of DCB-1 formed per part of the catalyst consumed.

The experiment was repeated without the addition of dimethyl phenylphosphonite. In this case, after about 25 hours only 80 parts of DCB-1 had formed, and approximately 75% of the catalyst had been consumed corresponding to a catalyst usage of only about 107 parts of DCB-1 formed per part of catayst consumed.

The growth of DCB-1 was monitored by g.l.c. throughout the experiments, and the results are shown graphically in FIG. 1 of the accompanying drawings, in which reaction time is plotted against growth of DCB-1.

In FIG. 1 curve A represents the Example and curve B the comparative experiment. The catalyst was added at point C on curve A.

It will be seen that after the pre-treatment with dimethyl phenylphosphonite the rate of growth of DCB-1 was much more rapid. In fact, the fall-off in curve A after about 25 hours was due more to the drop in the concentration of unconverted acrylonitrile than consumption of catalyst.

EXAMPLE 2

The procedure of Example 1 was repeated, but isopropyl bis(para)tolyphosphinite (1 part) was used as catalyst. A control experiment, omitting the scavenging reagent was also carried out. The results are illustrated graphically in FIG. 2 of the accompanying drawings. Reference letters A, B and C have the same significance as in FIG. 1.

What we claim is:

1. A two step process for the dimerisation of acrylonitrile to predominantly 1,4-dicyanobutenes, in which the acrylonitrile is dissolved in an organic solvent capable of donating protons, the acrylonitrile and solvent being substantially dry such that the water level of the reaction mixture is less than 50 ppm by volume, the acrylonitrile being present in a concentration of from 5% to 75% by volume, and the solution contacted at a temperature in the range of 0° C. to 180° C. with a catalyst comprising from 0.001 to 1% by volume of an aryl phosphinite of the formula:

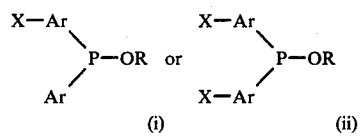

where Ar is a phenyl or a naphthyl group and where groups X, which may be the same or different, are electron-donating substituents of the aromatic nucleus which give rise to a negative Hammett σ constant, and R represents a cyclohexyl group or an alkyl group having 1 to 8 carbon atoms, the acrylonitrile and solvent being contacted in a first step with a scavenging reagent in the proportion of 0.02% to 1% by volume calculated on the total volume of the acrylonitrile/solvent mixture wherein said scavenging reagent is an aryl phosphonite containing two alkoxy groups or cycloalkoxy groups and one aryl group attached to the phosphorus atom wherein said aryl group is phenyl or tolyl, for a predetermined period of time before being contacted with the said catalyst to react said scavenging agent with residual impurities contained in said acrylonitrile/solvent reaction mixture and thereafter in a second discreet step contacting said acrylonitrile/solvent reaction mixture with said catalyst.

2. A process as claimed in claim 1, in which the substituent X, or at least one of the substituents X is in the para position.

3. A process as claimed in claim 1 or claim 2 in which the Ar group is a phenyl group.

4. A process as claimed in claims 1 or 2, in which the substituent X is selected from alkoxy groups, alkyl groups or alkylamino groups.

5. A process as claimed in claim 1 in which the scavenging reagent is a dialkyl phenylphosphonite or a dialkyl tolylphosphonite.

6. A process as claimed in claim 5 in which the scavenging reagent is dimethylphenylphosphonite or dimethyl tolylphosphonite.

* * * * *